United States Patent [19]

Wright et al.

[11] 4,291,163

[45] Sep. 22, 1981

[54] DECAHYDROQUINOLINE-2-CARBOXYLIC ACID COMPOUNDS

[75] Inventors: George C. Wright; Ronald E. White, both of Norwich, N.Y.

[73] Assignee: Morton-Norwich Products, Inc., Norwich, N.Y.

[21] Appl. No.: 114,675

[22] Filed: Jan. 23, 1980

[51] Int. Cl.³ .............................................. C07D 215/16
[52] U.S. Cl. .................................... 546/164; 424/258

[58] Field of Search ......................................... 546/164

*Primary Examiner*—Donald G. Daus
*Assistant Examiner*—D. B. Springer
*Attorney, Agent, or Firm*—Anthony J. Franze

[57] ABSTRACT

Certain decahydroquinoline-2-carboxylic acid compounds are useful as inhibitors of Angiotensin I converting enzyme.

1 Claim, No Drawings

DECAHYDROQUINOLINE-2-CARBOXYLIC ACID COMPOUNDS

This invention is concerned with decahydroquinoline-2-carboxylic acid compounds, particularly decahydro-1-(3-mercapto-1-oxopropyl)quinoline-2-carboxylic acid; its sodium salt; and the dicyclohexylamine salt of its benzoyl derivative.

These compounds are potent inhibitors of the enzyme responsible for converting the decapeptide Angiotensin I to the octapeptide Angiotensin II. The latter is the powerful pressor agent implicated as the causative agent in some forms of hypertension.

Of late, it has been recognized that a substance capable of interrupting the pathway whereby Angiotensin II is produced, viz; the conversion hereabove referred to, presents a useful and effective means of combating hypertension associated with that pressor agent.

It has been discovered that the compounds of this invention are possessed of noteworthy activity in inhibiting Angiotensin I converting enzyme. Thus, in vitro techniques designed to evince such activity these compounds are highly effective. For example, they inhibit the pure converting enzyme isolated from rabbit lung tissue at levels of from 0.061–0.18 $\mu$M. They are, therefore, notable Angiotensin I converting enzyme inhibitors.

The compounds of this invention are not limited to in vitro manifestations of their converting enzyme inhibiting propensity. Upon oral administration, a dose dependent antihypertensive effect in acute aortic coarctation hypertensive rats is elicited. Such oral dosage as, for example, a suspension in 0.5% Methocel solution to achieve an $ED_{30}$ (calculated oral dosage for a reduction of 30 mm Hg in mean arterial blood pressure) is about 10–200 mg/kg.

In order that this invention may be readily available to those skilled in the art, the currently preferred methods for the preparation of the compounds thereof are illustrated by the following examples:

EXAMPLE I 1-(3-Benzoylthio-1-oxopropyl)-decahydroquinoline-2-carboxylic Acid Dicyclohexylamine Salt Hemihydrate A mixture of quinoline-2-carboxylic acid (30 g, 0.17 mole), glacial acetic acid (1000 ml), and $PtO_2$ (2.0 g) was subjected to hydrogenation at room temperature for 3 hours using 51.7 psia $H_2$ (theory: 58.7 psia $H_2$). The catalyst was removed by filtration and the filtrate was stripped of solvent under reduced pressure. The residue was dissolved in acetonitrile (300 ml) and the mixture was cooled. The product was collected by filtration and washed with acetonitrile and ether; m.p. 254°–258°; yield: 20 g. The filtrate was diluted with ether, cooled, and the product was collected by filtration. The two products were combined to give 23 g (74%) of decahydroquinoline-2-carboxylic acid.

Anal. Calcd. for $C_{10}H_{17}NO_2$: C, 65.54; H, 9.35; N, 7.65. Found: C, 65.36; H, 9.38; N, 7.56.

A solution of NaOH (5.2 g, 0.13 mole) in $H_2O$ (130 ml) was added to decahydroquinoline-2-carboxylic acid (23 g, 0.13 mole) with stirring. The solution was cooled in an ice bath and a solution of 3-bromopropionyl chloride (22 g, 0.13 mole) in tetrahydrofuran (130 ml) and a solution of NaOH (5.2 g, 0.13 mole) in $H_2O$ (65 ml) were added simultaneously over 75 minutes at 2°–5°. The mixture was stirred at 2° for 30 minutes, the ice bath was removed, and the mixture was stirred at room temperature for 3½ hours. The mixture was cooled to 19° in an ice bath, a mixture of potassium thiobenzoate (23 g, 0.13 mole) in $H_2O$ (120 ml) was added, and the mixture was stirred for 17½ hours at room temperature. The mixture was diluted with $H_2O$ (150 ml), adjusted to pH 2 with concentrated HCl, and the product was extracted with $CHCl_3$ (3×300 ml). The $CHCl_3$ was stripped of solvent under reduced pressure. The residue was dissolved in acetonitrile (150 ml) and the solution was adjusted to pH 8 with dicyclohexylamine. The mixture was cooled, the product was collected by filtration and recrystallized from isopropanol (700 ml), yield: 28 g (38%). A sample was recrystallized from isopropanol, m.p. 173°–176°.

Anal. Calcd. for $C_{20}H_{25}NO_4S \cdot HN(C_6H_{11})_2 \cdot \frac{1}{2}H_2O$: C, 67.93; H, 8.73; N, 4.95; $H_2O$, 1.59. Found: C, 67.85; H, 8.98; N, 4.86; $H_2O$, 0.79.

EXAMPLE II

Decahydro-1-(3-mercapto-1-oxopropyl)quinoline-2-carboxylic Acid Tetartohydrate

Potassium bisulfate (27 g, 0.20 mole) was added to a mixture of the compound of Example I (57 g, 0.10 mole) in $H_2O$ (800 ml) and chloroform (500 ml) at 26°. The mixture was stirred for 30 minutes at room temperature, the $CHCl_3$ layer was separated, the aqueous phase was extracted with $CHCl_3$ (200 ml) and the $CHCl_3$ extracts were combined. The extract was dried over $MgSO_4$, filtered and the filtrate was stripped of solvent under reduced pressure. The oily residue was cooled to 7° in an ice bath and a solution of concentrated ammonium hydroxide (65 ml) and $H_2O$ (130 ml) was added, with a temperature rise to 22°. The mixture was cooled to 15°, the ice bath was removed and the mixture was stored for 3 hours at ambient temperature (the reaction was run under a blanket of nitrogen). The mixture was filtered and the filtrate was diluted with water (180 ml). The solution was extracted with ethyl acetate (2×200 ml), the aqueous phase was cooled in an ice bath to 6° and the solution was adjusted to pH 2 with concentrated HCl. The product was extracted with $CHCl_3$ (2×300 ml), the extract was dried over $Na_2SO_4$ and Darco and the mixture was filtered. The filtrate was stripped of solvent under reduced pressure, the residue was cooled and became semi-crystalline. The residue was washed in anhydrous ether (40 ml) and the product was collected by filtration; m.p. 131°–133°, yield: 8.5 g (31%).

Anal. Calcd. for $C_{13}H_{21}NO_3S \cdot \frac{1}{4}H_2O$: C, 56.60; H, 7.86; N, 5.08; $H_2O$, 1.63. Found: C, 56.79; H, 7.48; N, 4.97; $H_2O$, 3.34.

EXAMPLE III

Decahydro-1-(3-mercapto-1-oxopropyl)quinoline-2-carboxylic Acid Sodium Salt Hydrate A mixture of the compound of Example II (4.5 g, 0.016 mole) and isopropanol (50 ml) was cooled in an ice bath to 5°. The mixture was adjusted to pH 6–7 with 31 ml of a solution of 2% of NaOH/absolute alcohol. The solution was stripped of solvent under reduced pressure, the residue was heated in acetonitrile (130 ml), and the mixture was cooled overnight. The product was collected by filtration and washed with acetonitrile and ether; m.p. 144°–149°, yield: 3.5 g (73%).

Anal. Calcd. for $C_{13}H_{20}NNaO_3S\cdot\frac{3}{8}H_2O$: C, 52.05; H, 6.92; N, 4.67; $H_2O$, 2.25. Found: C, 52.13; H, 7.04; N, 4.74; $H_2O$, 5.3.

What is claimed is:

1. A compound selected from the group consisting of:
   A. 1-(3-Benzoylthio-1-oxopropyl-decahydroquinoline-2-carboxylic acid dicyclohexylamine salt hemihydrate,
   B. Decahydro-1-(3-mercapto-1-oxopropyl)quinoline-2-carboxylic acid tetartohydrate; and
   C. Decahydro-1-(3-mercapto-1-oxopropyl)quinoline-2-carboxylic acid sodium salt $\frac{3}{8}$ hydrate.